(12) United States Patent
Minogue et al.

(10) Patent No.: US 6,885,896 B2
(45) Date of Patent: Apr. 26, 2005

(54) ELECTROTHERAPY DEVICE AND METHOD

(75) Inventors: Michael Conor Minogue, Kinvara (IE); Michael Louis Crowe, Dublin (IE)

(73) Assignee: Bio-Medical Research Ltd., Galway (IE)

( * ) Notice: Subject to any disclaimer, the term of this patent is extended or adjusted under 35 U.S.C. 154(b) by 79 days.

(21) Appl. No.: 09/902,281

(22) Filed: Jul. 10, 2001

(65) Prior Publication Data

US 2002/0091420 A1 Jul. 11, 2002

Related U.S. Application Data

(63) Continuation of application No. PCT/IE00/00004, filed on Jan. 11, 2000.

(30) Foreign Application Priority Data

Jan. 11, 1999 (IE) .......................................... S1999/0016

(51) Int. Cl.$^7$ ................................................. A61N 1/08
(52) U.S. Cl. ......................................... 607/48; 607/148
(58) Field of Search ............................. 607/48, 72, 115, 607/148–149, 152; 600/372, 382, 390, 393; 482/1–2

(56) References Cited

U.S. PATENT DOCUMENTS

| | | |
|---|---|---|
| 194,520 A | 8/1877 | Hobbs |
| 226,658 A | 4/1880 | Graydon |
| 276,078 A | 4/1883 | Rittig |
| 279,881 A | 6/1883 | Palmer |
| 372,647 A | 11/1887 | Williams |
| 880,041 A | 2/1908 | Renton |
| 2,110,392 A | 3/1938 | Dorr |
| 2,711,729 A | 6/1955 | Hofmann |
| 2,943,628 A | 7/1960 | Howell |
| 3,409,007 A | 11/1968 | Fuller |
| 3,534,727 A | 10/1970 | Roman |
| 3,610,250 A | 10/1971 | Sarbacher |
| 3,881,495 A | 5/1975 | Pannozzo et al. ............ 128/422 |
| 4,354,509 A | 10/1982 | Strahwald et al. ........... 128/803 |
| 4,365,634 A | 12/1982 | Bare et al. ................... 128/640 |

(Continued)

FOREIGN PATENT DOCUMENTS

| | | |
|---|---|---|
| DE | 20 14 944 | 10/1971 |
| EP | 0 603 452 | 6/1994 |
| EP | 0 830 875 | 3/1998 |
| EP | 0 847 776 | 6/1998 |
| FR | 2 190 482 | 2/1974 |
| FR | 2 342 082 | 9/1977 |
| WO | WO 90/04955 | 5/1990 |

Primary Examiner—Mark Bockelman
(74) Attorney, Agent, or Firm—Frommer Lawrence & Haug LLP; Nathan D. Weber, Esq.

(57) ABSTRACT

A device for attaching at least three electrodes to a subject for stimulating abdominal muscles of the subject. The device comprises an attachment mechanism for extending around the torso of the subject and a main locating element on the attachment mechanism for locating a central electrode of the at least three electrodes adjacent the umbilicus of the subject. Two secondary locating elements are also provided on the attachment mechanism disposed on respective opposite sides of the main locating element for locating two corresponding side electrodes of the at least three electrodes spaced apart from the central electrode in a general direction towards a corresponding one of the right and left midaxillary lines of the torso intermediate the rib cage and corresponding right and left iliac crests. By applying at least one pulsed signal to the subject through the respective central and side electrodes, abdominal muscles of the subject are stimulated.

64 Claims, 10 Drawing Sheets

U.S. PATENT DOCUMENTS

| | | | |
|---|---|---|---|
| 4,381,012 A | 4/1983 | Russek | 128/644 |
| 4,381,789 A | 5/1983 | Naser et al. | 128/798 |
| 4,422,461 A | 12/1983 | Glumac | 128/798 |
| 4,432,368 A | 2/1984 | Russek | 128/644 |
| 4,509,535 A | 4/1985 | Bryan | 128/798 |
| 4,556,214 A | 12/1985 | Petrofsky et al. | 272/117 |
| 4,580,569 A | 4/1986 | Petrofsky | |
| 4,583,547 A | 4/1986 | Granek et al. | 128/639 |
| 4,633,888 A | 1/1987 | Yoneyama | 128/784 |
| 4,690,146 A | 9/1987 | Alon | |
| 4,708,149 A | 11/1987 | Axelgaard et al. | 128/798 |
| 4,729,377 A | 3/1988 | Granek et al. | 128/639 |
| 4,763,660 A | 8/1988 | Kroll et al. | 128/640 |
| 4,856,525 A | 8/1989 | van den Honert | |
| 5,190,036 A * | 3/1993 | Linder | 607/42 |
| 5,263,481 A | 11/1993 | Axelgaard | 128/640 |
| 5,336,255 A | 8/1994 | Kanare et al. | 607/149 |
| 5,344,440 A | 9/1994 | Stephen | 607/139 |
| 5,397,337 A | 3/1995 | Jaeger et al. | 607/62 |
| 5,397,338 A | 3/1995 | Grey et al. | 607/115 |
| 5,443,494 A | 8/1995 | Paolizzi et al. | 607/149 |
| 5,487,759 A | 1/1996 | Bastyr et al. | 607/149 |
| 5,601,618 A | 2/1997 | James | 607/71 |
| 5,622,168 A | 4/1997 | Keusch et al. | 128/640 |
| 5,674,261 A | 10/1997 | Smith | 607/46 |
| 5,823,989 A | 10/1998 | Ostrow | 604/20 |
| 5,871,534 A | 2/1999 | Messick et al. | 607/138 |
| 5,904,712 A | 5/1999 | Axelgaard | 607/148 |
| 5,916,159 A | 6/1999 | Kelly et al. | 600/390 |
| 5,922,012 A | 7/1999 | Sakano | 607/46 |
| 5,947,897 A | 9/1999 | Otake | 600/372 |
| 5,995,861 A | 11/1999 | Price | 600/37 |
| 6,002,965 A | 12/1999 | Katz et al. | 607/48 |
| D420,138 S | 2/2000 | Robinette | D24/200 |
| 6,094,599 A | 7/2000 | Bingham et al. | 607/149 |
| 6,151,528 A | 11/2000 | Maida | 607/149 |
| 6,324,432 B1 | 11/2001 | Rigaux et al. | 607/62 |
| 6,341,237 B1 | 1/2002 | Hurtado | 607/148 |
| 6,438,428 B1 * | 8/2002 | Axelgaard et al. | 607/152 |

* cited by examiner

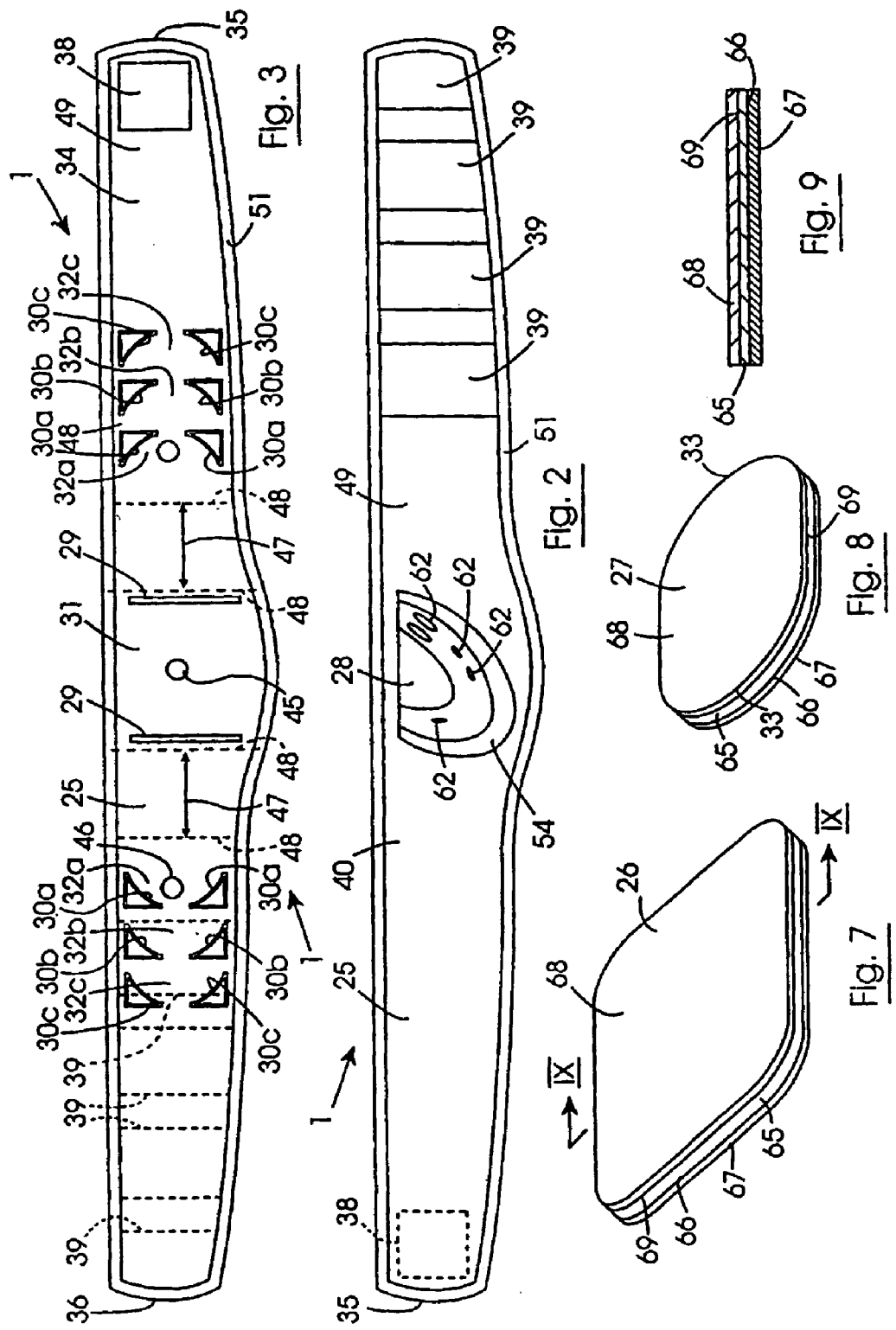

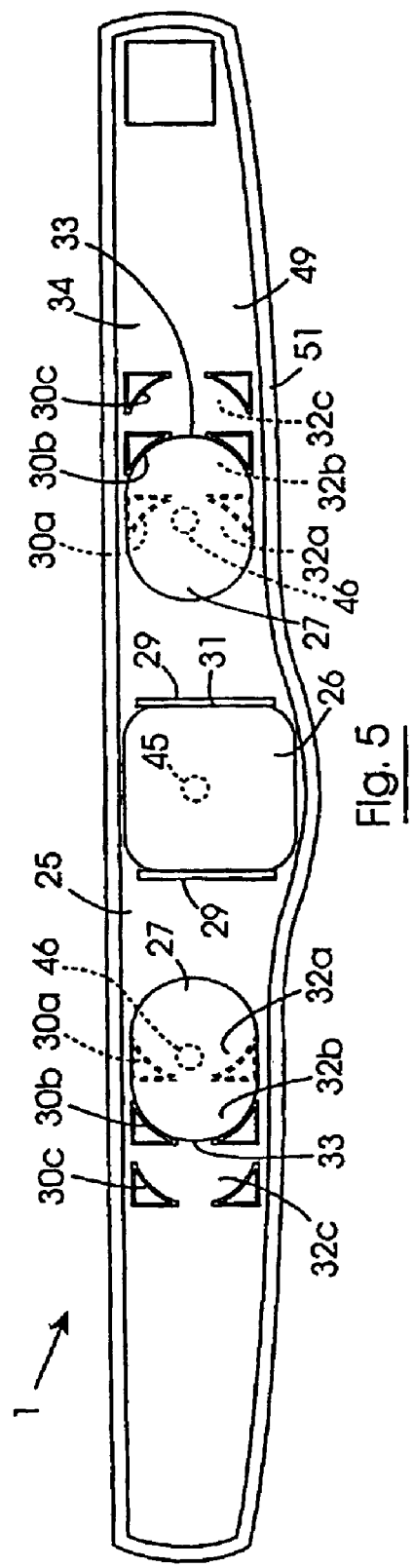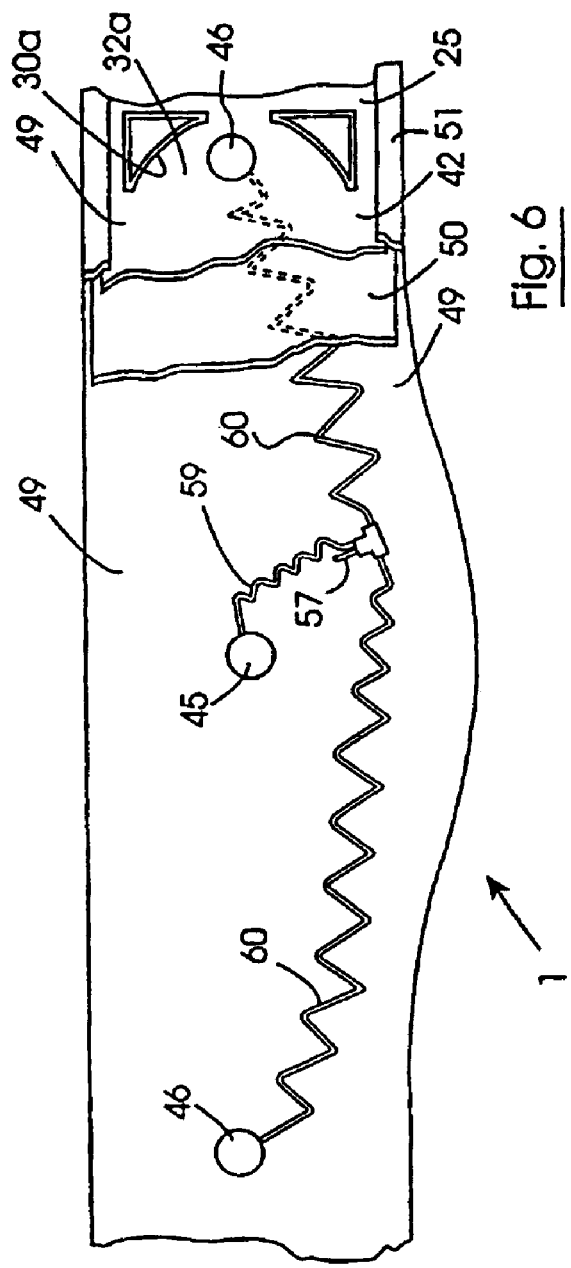

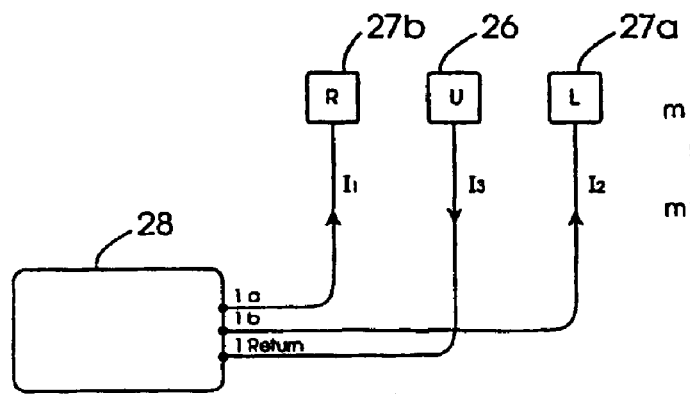 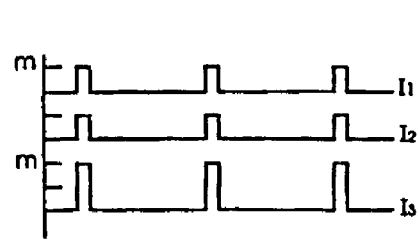
Fig. 13        Fig. 14
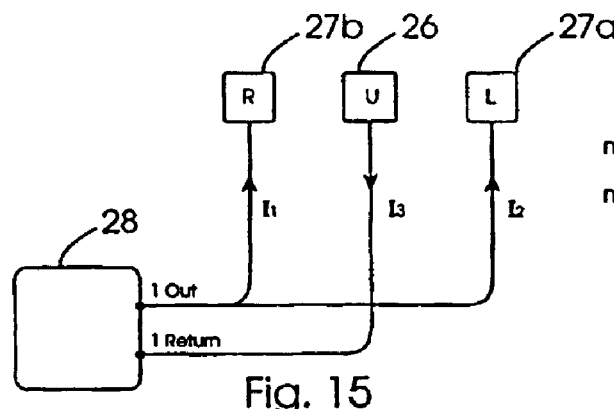 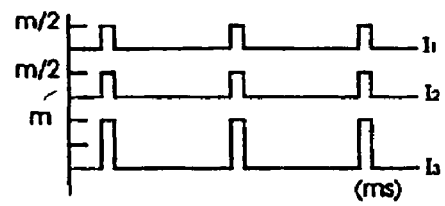
Fig. 15        Fig. 16
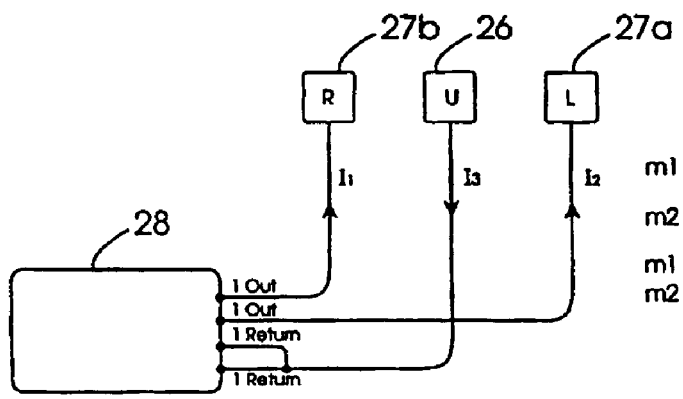 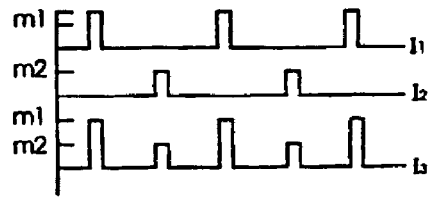
Fig. 17        Fig. 18

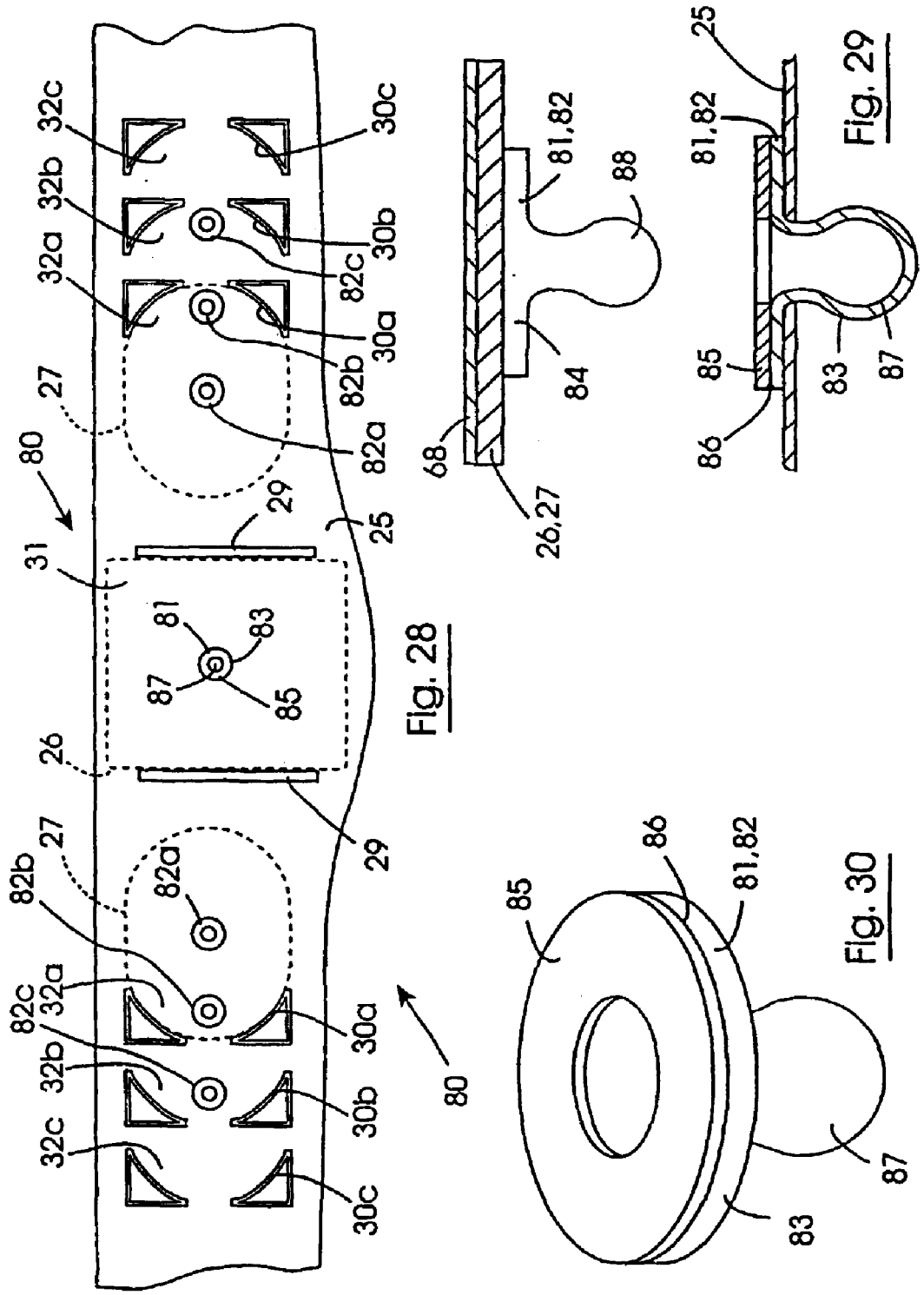

ELECTROTHERAPY DEVICE AND METHOD

CROSS REFERENCE TO RELATED APPLICATIONS

This application is a continuation of application of PCT/IE00/00004, filed on Jan. 11, 2000 which claims the benefit of priority to Irish Application No. S1999/0016, filed on Jan. 11, 1999.

BACKGROUND OF THE INVENTION

1. Filed of the Invention

The present invention relates to a device for attaching electrodes to a subject for stimulating abdominal muscles by electrotherapy, and the invention also relates to a device for stimulating abdominal muscles by electrotherapy. The invention further relates to an electrotherapeutic method for stimulating abdominal muscles, and to a fastener for use in the device.

2. Description of the Prior Art

Electrotherapy is commonly used for stimulating abdominal muscles for improving and toning the muscles, and for the relief of pain. Known electrotherapeutic methods and devices require that a pulsed signal be passed subcutaneously through the subject between a pair of electrodes which typically, are aligned with the muscle to be stimulated for defining a current path between the electrode which is co-linear with the direction of the muscle. In known electrotherapeutic devices and methods, it is necessary to provide a relatively large number of electrode pairs for stimulating the more important abdominal muscles, for example, the central rectus abdominis muscle, and the transversalis and oblique muscles. Typically, one or two pairs of electrodes are required located on respective opposite sides of the umbilicus for stimulating the rectus abdominis muscle, and two obliquely located electrode pairs are required towards the respective sides of the abdominal region for stimulating the transversalis and oblique muscles on the respective sides of the abdomen. Thus, in order to stimulate the rectus abdominis muscle, the transversalis and oblique muscles, three to four electrode pairs are required. This, leads to a number of disadvantages, in that firstly, unless extreme care is taken in locating the electrodes on the abdomen of the subject some or all of the electrodes can readily easily be misaligned with the respective muscles or displaced therefrom, thus, leading to significant inefficiencies and indeed in extreme cases ineffectual treatment. Secondly, because of the high number of electrode pairs, a relatively complex signal generator is required for providing appropriately pulsed signals so that the pulsed signals only travel between the respective pairs between which the pulsed signals are to travel subcutaneously in the subject. Thirdly, in many cases there is a danger of transthoracic current paths being defined by the electrodes, which in certain cases can lead to transthoracic currents within the subject, which in extreme cases may cause cardiac arrhythmias. The possibility of misalignment of the electrode pairs further increases the risk of transthoracic currents being passed through the subject.

There is therefore a need for a device for attaching electrodes to a subject for stimulating abdominal muscles and in particular for stimulating the rectus abdominis, the transversalis and the oblique muscles, which overcomes these problems. There is also a need for an electrotherapeutic device and a method for stimulating abdominal muscles which overcomes these problems.

SUMMARY OF THE INVENTION

The present invention is directed towards providing such a device for attaching electrodes to a subject, such an electrotherapeutic device and method for stimulating abdominal muscles of a subject. The invention is also directed towards providing a fastener for use in the device.

According to the invention there is provided a device for attaching at least three electrodes to a subject for stimulating abdominal muscles of the subject, the device comprising an attachment means for extending around the torso of the subject, wherein a main locating means is provided on the attachment means for locating a central electrode of the at least three electrodes adjacent the umbilicus of the subject, and two secondary locating means are provided on the attachment means disposed on respective opposite sides of the main locating means for locating two corresponding side electrodes of the at least three electrodes spaced apart from the central electrode in a general direction towards a corresponding one of the left and right mid-axillary lines of the torso intermediate the rib cage and corresponding left and right iliac crests so that by applying at least one pulsed signal to the subject through the respective central and side electrodes abdominal muscles of the subject are stimulated.

In one embodiment of the invention the secondary locating means are disposed on the attachment means for locating the respective side electrodes towards the mid-point of the corresponding mid-axillary line between the rib cage and the corresponding iliac crest. Preferably, the secondary locating means are disposed on the attachment means for locating the respective side electrodes adjacent the corresponding mid-axillary line.

Ideally, the secondary locating means are disposed on the attachment means for locating the respective side electrodes adjacent the mid-point of the corresponding mid-axillary line between the rib cage and the corresponding iliac crest.

Preferably, the main locating means is disposed on the attachment means for locating the central electrode on the umbilicus and extending around the umbilicus. Advantageously, the main locating means is disposed on the attachment means for locating the central electrode on the umbilicus and extending completely around the umbilicus.

In one embodiment of the invention the main locating means is disposed on the attachment means for locating the central electrode on the umbilicus, but with a greater area of the central electrode located below the umbilicus than above the umbilicus.

In another embodiment of the invention the main locating means is disposed on the attachment means for locating the central electrode adjacent but not on the umbilicus.

In a further embodiment of the invention the main locating means is disposed on the attachment means for locating the central electrode below the umbilicus.

In a still further embodiment of the invention the main locating means is disposed on the attachment means for locating the central electrode above the umbilicus.

In a further embodiment of the invention the main locating means is disposed on the attachment means for locating the central electrode both below and above the umbilicus.

In one embodiment of the invention a reference means is provided on the attachment means for locating the attachment means on the torso relative to an anatomical reference. Preferably, the reference means is provided for locating the attachment means circumferentially around the torso. Advantageously, the reference means is provided for locating the attachment means vertically along the torso.

In one embodiment of the invention the main locating means acts as the reference means for locating the attachment means relative to the anatomical reference provided by the umbilicus.

In another embodiment of the invention the main locating means comprises a first main locating means and a second main locating means for locating respective corresponding first and second central electrodes adjacent the umbilicus of the subject.

Advantageously, the first main locating means is provided for locating the first central electrode above the umbilicus, and the second main locating means is provided for locating the second central electrode below the umbilicus.

In another embodiment of the invention two sets of at least two secondary locating means are disposed on the respective opposite sides of the main locating means for facilitating selective location of the respective side electrodes for accommodating different girths of torso.

Advantageously, each set of secondary locating means comprises three secondary locating means.

In another embodiment of the invention portions of the attachment means on respective opposite sides of the main locating means between the main locating means and the corresponding secondary locating means are of resilient material for facilitating resilient stretching of the attachment means between the main and corresponding secondary locating means. Preferably, the attachment means is of a resilient material for facilitating stretching of the attachment means around the torso, the resilient portions of the attachments means being of greater stretchability than that of the rest of the attachment means.

In one embodiment of the invention a main electrically conductive contact means is provided on the attachment means corresponding to each main locating means for receiving the at least one pulsed signal and for relaying the signal to the corresponding central electrode. Preferably, each main contact means is located within the corresponding main locating means.

In another embodiment of the invention two secondary electrically conductive contact means are provided on the attachment means for receiving the at least one pulsed signal and for relaying the signal to the respective corresponding side electrodes. Advantageously, each secondary contact means is located adjacent the corresponding secondary locating means or the corresponding set of secondary locating means.

In another embodiment of the invention each secondary contact means is located adjacent the corresponding set of secondary locating means so that irrespective of which secondary locating means is selected for locating the corresponding side electrode the side electrode is in electrically conductive engagement with the secondary contact means.

Advantageously, each main and secondary locating means is provided by a visually perceptive locating means. Preferably, each main and secondary locating means is formed by a corresponding locating mark on the attachment means.

Ideally, each locating mark defines an outline of a part of the periphery of the corresponding electrode corresponding to the locating means.

In one embodiment of the invention each locating means is adapted for locating a patch type electrode.

In another embodiment of the invention the device comprises the at least three electrodes. Preferably, each electrode is a patch type electrode.

In one embodiment of the invention each side electrode is sized to cover at least a portion of the corresponding lower thoracic nerves and the corresponding first and second lumbar nerves.

In another embodiment of the invention each central electrode is sized to extend substantially across the rectus abdominus muscle.

Advantageously, each electrode defines an area of contact over which the electrode makes direct electrical contact with the subject, the area of contact of each side electrode being such as not to exceed the area of contact of the or both central electrodes. Preferably, the area of contact of each side electrode does not exceed one third of the area of contact of the or both central electrodes.

In one embodiment of the invention each side electrode is of width in a circumferential direction relative to the torso of the subject in the range of 50 mm to 150 mm, and is of length in a vertical direction relative to the torso of the subject in the range of 80 mm to 120 mm.

In one embodiment of the invention a first electrically conductive coating is provided on one side of each electrode for electrically connecting the electrode to the corresponding contact means. Advantageously, the first coating is a gel type coating containing an electrolyte solution for enhancing electrical contact between the electrode and the corresponding contact means.

In another embodiment of the invention a second electrically conductive coating is provided on the other side of each electrode for electrically connecting the patch electrode and the torso of the subject. Preferably, the second coating is a gel type coating.

In one embodiment of the invention the second coating is an adhesive coating.

In another embodiment of the invention the first coating is an adhesive coating.

Advantageously, the bond strength of the first coating to the attachment means is greater than the bond strength of the second coating to the torso for facilitating removal of the attachment means and the electrodes located thereon from the torso of the subject.

Preferably, the electrodes are pre-coated with the respective first and second adhesive coatings.

In one embodiment of the invention a receiving means is provided in the attachment means for receiving a signal generating means for generating the at least one pulsed signal.

Preferably, a main electrical connecting means extends between the receiving means and each main contact means for relaying the at least one pulsed signal from the signal generating means to the corresponding main contact means.

Advantageously, a secondary electrical connecting means extends between the receiving means and each secondary contact means for relaying the at least one pulsed signal from the signal generating means to the corresponding secondary contact means.

Ideally, each electrical connecting means is located within the attachment means.

In one embodiment of the invention the receiving means is a releasable receiving means for releasably receiving the signal generating means.

Advantageously, the receiving means receives the signal generating means with a snap fit action.

In one embodiment of the invention the signal generating means for generating the at least one pulsed signal is provided in the receiving means.

In one embodiment of the invention a means is provided for selectively selecting at least one pair of electrodes from the at least three electrodes through which the at least one pulsed signal is applied to the subject.

In another embodiment of the invention the at least one pulsed signal is applied simultaneously to each of the selected pairs of electrodes. Alternatively, the at last one pulsed signal is applied sequentially to each of the selected pairs of electrodes.

In one embodiment of the invention one of the selected pairs of the electrodes comprises one side electrode and the central electrode, and another selected pair of the electrodes comprises the other side electrode and the central electrode.

In another embodiment of the invention one of the selected pairs of electrodes comprises the two side electrodes.

In another embodiment of the invention one of the selected pairs of electrodes comprises one of the side electrodes and one of the first and second central electrodes, and another of the selected pairs of electrodes comprises the other of the side electrodes and the other of the first and second central electrodes.

In a further embodiment of the invention one of the selected pairs of electrodes comprises the first and second central electrodes which act as one single electrode and one of the side electrodes, and another of the selected pairs of electrodes comprises the first and second central electrodes which act as one single electrode and the other side electrode.

In a still further embodiment of the invention one of the selected pairs of electrodes comprises the first and second central electrodes.

In one embodiment of the invention the pulsed signals generated by the signal generating means for applying to the respective pairs of electrodes may be the same or different.

In one embodiment of the invention each pulsed signal comprises a plurality of pulses at intervals in the range of 5 milliseconds to 1000 milliseconds. Preferably, each pulsed signal comprises a plurality of pulses at intervals in the range of 20 milliseconds to 40 milliseconds.

Advantageously, each pulsed signal comprises a plurality of pulses at intervals of approximately 30 milliseconds±20%. Preferably, the interval between pulses of each pulsed signal is adjustable.

In another embodiment of the invention each pulsed signal comprises pulses of duration in the range of 10 microseconds to 200000 microseconds. Advantageously, each pulsed signal comprises pulses of duration in the range of 50 microseconds to 1000 microseconds.

Preferably, each pulsed signal comprises pulses of duration in the range of 100 microseconds to 500 microseconds. Ideally, each pulsed signal comprises pulses of duration of approximately 300 milliseconds±20%. Preferably, the duration of each pulsed signal is adjustable.

In another embodiment of the invention each pulsed signal comprises a plurality of pulses of magnitude in the range of 0 mA to 100 mA. Preferably, the magnitude of each pulse of each pulsed signal is adjustable.

In one embodiment of the invention the attachment means comprises a belt.

In another embodiment of the invention a securing means is provided on the belt for securing the belt around the torso of the subject.

In a further embodiment of the invention a main fastening means is provided corresponding to each main locating means for fastening a corresponding central electrode to the attachment means adjacent the corresponding main locating means.

In a still further embodiment of the invention two secondary fastening means are provided in the attachment means for fastening the respective side electrodes to the attachment means adjacent the corresponding selected secondary locating means.

In one embodiment of the invention each fastening means comprises a stud fastener.

In another embodiment of the invention each stud fastener comprises a female part and a male part, the female part being secured to the attachment means.

In a further embodiment of the invention each stud fastener is electrically conductive so that the female part of the stud fasteners form the corresponding contact means.

Preferably, an exposed surface of the female part of each stud fastener is of electrically insulating material.

Advantageously, the exposed surface of each female part of each stud faster is coated with an electrically insulating coating.

Additionally, the invention provides a stud fastener for use in the device according to the invention, the stud fastener comprises a male part for attaching to a corresponding electrode, and a female part for attaching to the attachment means.

In one embodiment of the invention the male and female parts of the stud fastener engage each other with electrically conductive engagement.

In another embodiment of the invention an exposed external surface of the female part of the stud fastener which abuts the male part of the stud fastener is of electrically insulating material.

In a further embodiment of the invention the electrically insulating material is provided by an electrically insulated coating on the exposed abutting surface.

The invention further provides a method for stimulating abdominal muscles of a subject, the method comprising passing at least one pulsed signal subcutaneously through the subject between selected electrodes of at least three electrodes, one of the at least three electrodes being a central electrode located adjacent the umbilicus of the subject, and the other two electrodes being side electrodes located on the subject spaced apart from the central electrode on respective sides thereof in a general direction towards a corresponding one of the left and right mid-axillary lines of the torso intermediate the rib cage and corresponding left and right iliac crests.

In one embodiment of the invention each side electrode is located towards the mid-point of the corresponding mid-axillary line between the rib cage and the corresponding iliac crest. Preferably, each side electrode is located adjacent the corresponding mid-axillary line. Ideally, each side electrode is located adjacent the mid-point of the corresponding mid-axillary line between the rib cage and the corresponding iliac crest.

Preferably, the central electrode is located on the umbilicus and extends around the umbilicus. Advantageously, the central electrode is located on the umbilicus and extends completely around the umbilicus.

In one embodiment of the invention the central electrode is located on the umbilicus, but with a greater area of the central electrode located below the umbilicus than above the umbilicus.

In another embodiment of the invention the central electrode is located adjacent but not on the umbilicus.

In a further embodiment of the invention the central electrode is located below the umbilicus.

In a still further embodiment of the invention the central electrode is located above the umbilicus.

In another embodiment of the invention the central electrode is located both below and above the umbilicus.

In a still further embodiment of the invention the central electrode is provided by two electrodes, namely, a first central electrode and a second central electrode, both of which are located adjacent the umbilicus. Preferably, the first central electrode is located above the umbilicus and the second central electrode is located below the umbilicus.

In one embodiment of the invention the at least one pulsed signal is applied to the subject so that the signal passes subcutaneously through the subject between at least one selected pair of the at least three electrodes.

In one embodiment of the invention the at least one pulsed signal is applied simultaneously to each of the selected pairs of electrodes. Alternatively, the at last one pulsed signal is applied sequentially to each of the selected pairs of electrodes.

In one embodiment of the invention one of the selected pairs of electrodes comprises one side electrode and the central electrode, and another selected pair of electrodes comprises the other side electrode and the central electrode.

In another embodiment of the invention one of the selected pairs of electrodes comprises the two side electrodes.

In a further embodiment of the invention one of the selected pairs of electrodes comprises one of the side electrodes and one of the first and second central electrodes, and another of the selected pairs comprises the other of the side electrodes and the other of the first and second central electrodes.

In a still further embodiment of the invention one of the selected pairs of electrodes comprises the first and second central electrodes which act as one single electrode and one of the side electrodes, and another of the selected pairs of electrodes comprises the first and second central electrodes which act as one single electrode and the other side electrode.

In a further embodiment of the invention one of the selected pairs of electrodes comprises the first and second central electrodes.

In one embodiment of the invention the pulsed signals applied to the respective pairs of electrodes may be the same or different.

In one embodiment of the invention each pulsed signal comprises a plurality of pulses at intervals in the range of 5 milliseconds to 1000 milliseconds. Preferably, each pulsed signal comprises a plurality of pulses at intervals in the range of 20 milliseconds to 40 milliseconds. Advantageously, each pulsed signal comprises a plurality of pulses at intervals of approximately 30 milliseconds±20%.

Ideally, the interval between pulses of each pulsed signal is adjustable.

In one embodiment of the invention each pulsed signal comprises pulses of duration in the range of 10 microseconds to 200000 microseconds. Preferably, each pulsed signal comprises pulses of duration in the range of 50 microseconds to 1000 microseconds.

Advantageously, each pulsed signal comprises pulses of duration in the range of 100 microseconds to 500 microseconds. Ideally, each pulsed signal comprises pulses of duration of approximately 300 milliseconds±20%. Preferably, the duration of each pulsed signal is adjustable.

In another embodiment of the invention each pulsed signal comprises a plurality of pulses of magnitude in the range of 0 mA to 100 mA. Preferably, the magnitude of each pulse of each pulsed signal is adjustable.

Further the invention provides an electrotherapeutic device for stimulating muscles of a muscle group of a subject, the device comprising a plurality of electrodes for placing on the subject for applying at least one pulsed signal to the subject for stimulating the muscles, a signal generating means for generating the at least one pulsed signal, and a selecting means for selectively selecting the electrodes in electrode pairs and for selectively applying the at least one pulsed signal to the selected electrode pairs for selective stimulation of the muscles of the muscle group.

In one embodiment of the invention the selecting means comprises a switching means for selectively switching the at least one pulsed signal from the signal generating means to the electrodes.

Additionally, the invention provides a method for stimulating muscles of a muscle group of a subject, the method comprising passing at least one pulsed signal subcutaneously through the subject between selected electrodes of at least three electrodes, wherein the electrodes are selectively selected in electrode pairs for selectively stimulating selected muscles of the muscle group.

In one embodiment of the invention the electrode pairs are sequentially selected from the electrodes. Alternatively, the electrode pairs are simultaneously selected from the electrodes.

The advantages of the invention are many. An important advantage of the invention is that it permits relatively accurate placement and alignment of the electrodes on the subject. A particularly important advantage of the invention results from the fact that the device according to the invention permits relatively accurate placement of the electrodes on the subject, and because of this, it has been found that with only three electrodes the device according to the invention provides adequate stimulation to the abdominal muscles, and in particular, to the rectus abdominis and the transversalis and oblique muscles, particularly, for the purpose of toning the muscles. It has been surprisingly found that by locating the central electrode adjacent the umbilicus, and the respective side electrodes towards the corresponding mid-axillary lines to the respective left and right sides of the central electrode good stimulation of the abdominal muscles is achieved. However, it has been found that the closer the side electrodes are located to the corresponding left and right mid-axillary lines the better will be the stimulation. Indeed, it has been found that optimum stimulation is achieved by locating the respective side electrodes on corresponding lines extending from the umbilicus to the mid-point on the corresponding left and right mid-axillary lines between the rib cage and the corresponding iliac crest. In general, it has been found the maximum stimulation of the rectus abdominis, the transversalis and the oblique muscles is achieved when the side electrodes are located on the corresponding mid-axillary line substantially midway between the rib cage and the iliac crest. A further advantage of the invention is achieved where first and second central electrodes are provided, one above and the other below the umbilicus where it has been found that even greater stimulation of the abdominal muscles is achieved, and in particular, stimulation of the rectus abdominis, the transversalis and the oblique muscles.

By providing the side electrodes adjacent the mid-axillary line or spaced part from the central electrode towards the mid-axillary line, but relatively close to the mid-axillary line the side electrodes apply the pulsed signal or signals to nerve trunks rather than nerve branches which spread out from the nerve trunks. The electrical signals being applied to the nerve trunks, thus spread out through the nerve branches from the nerve trunks, and are thus effective in stimulating a significantly greater area of the muscles of the abdomen than if the electrodes were placed over nerve branches as has been the case heretofore. Additionally by placing the central electrode over or adjacent the umbilicus, and the side electrodes adjacent or relatively close to the mid-axillary line, the spacing between the central and side electrodes is such as to cause the pulsed signal or signals to travel deeper through the subject beneath the fatty tissue. This, thus, results in the pulsed signal or signals being targeted at the deeper muscle controlling nerves, thus providing more efficient stimulation of the muscles. Placing the electrodes relatively closely together, as has been the case heretofore, tends to cause the pulsed signal or signals to pass relatively near the surface of the skin, thus having little affect on the deeper muscle controlling nerves. Indeed, a further advantage of spacing the electrodes apart according to the invention is that the effect of subcutaneous currents on the touch and pain nerves is minimised, thereby minimising discomfort to the subject. Additionally, by providing the side electrodes of size to extend across the lower thoracic nerves and the first lumbar nerves adjacent the mid-axillary line further efficiency is achieved by virtue of the fact that the pulsed signal or signals is applied to the nerve trunks of these nerves. A further advantage of providing the electrodes of reasonable size is that the current density of the pulsed signal or signals passing through the electrodes, and in turn into the subject is minimised, thus, further minimising discomfort resulting from the effect of the subcutaneous current on the touch and pain nerves. Indeed, by providing the electrodes of reasonable size, a higher current may also be applied through the electrodes if such should be desired with minimum discomfort to the subject.

A further advantage of the invention is that it is virtually impossible to incorrectly attach or misapply the electrodes to the subject, and furthermore, there is virtually no danger of the pulsed signals being applied to the wrong electrodes, since the attachment means is pre-wired with the main and secondary connecting means.

A further advantage of the invention is achieved when provision is made for selectively selecting the electrodes into electrode pairs, in that individual muscles of muscle groups may be selectively stimulated, and additionally, if desired different pulsed signals may be applied to different selected electrode pairs.

The invention will be more clearly understood from the following description of some preferred embodiments thereof which are given by way of example only with reference to the accompanying drawings, in which:

BRIEF DESCRIPTION OF THE FIGURES

FIG. 2 is a front plan view of a device according to the invention for stimulating abdominal muscles, FIG. 3 is a rear plan view of the device of FIG. 2, FIG. 5 is a rear plan view of a portion of the device of FIG. 2 illustrating electrode pads positioned on the device, FIG. 6 is a cut-away rear plan view of another portion of the device of FIG. 2, FIGS. 7 and 8 are perspective views of respective electrodes of the device of FIG. 2, FIG. 9 is a transverse cross-sectional view of the electrode of FIG. 7 on the line IX—IX of FIG. 7, FIG. 13 is a block representation of a circuit of the device of FIG. 2, FIG. 14 is a graphical representation of pulsed signals generated by the device of FIG. 2, FIG. 15 is a block representation of an alternative circuit arrangement of the device of FIG. 2, FIG. 16 is a graphical representation of pulsed signals generated by the device of FIG. 2 in the configuration of FIG. 15, FIG. 17 is a block representation of an alternative circuit arrangement of the device of FIG. 2, FIG. 18 is a graphical representation of pulsed signals generated by the device of FIG. 2 in the configuration of FIG. 17, FIG. 28 is a rear plan view of a device according to another embodiment of the invention for stimulating abdominal muscles, FIG. 29 is an exploded transverse cross-sectional view of a detail of the device of FIG. 28, and FIG. 30 is a perspective view of a portion of a detail of the device of FIG. 28.

DETAILED DESCRIPTION OF THE PREFERRED EMBODIMENTS

Figures 22, 23, 24:
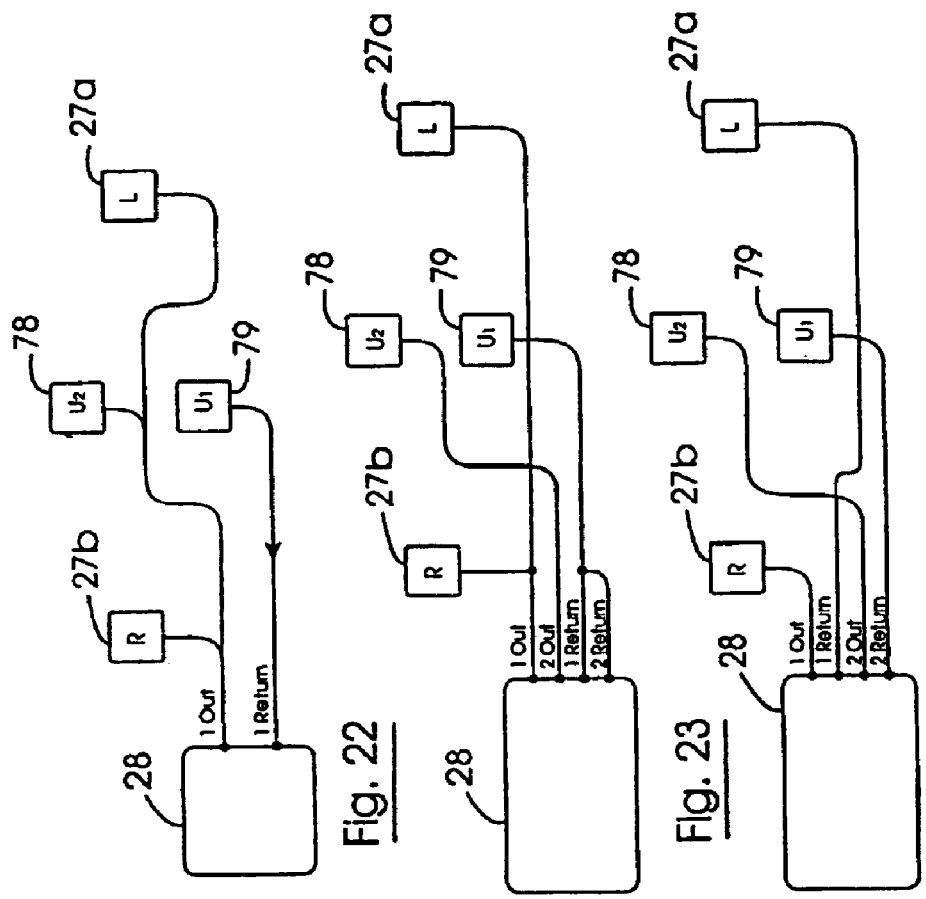

Referring to the drawings and initially to FIGS. 1 to 18 there is illustrated an electrotherapeutic device according to the invention indicated generally by the reference numeral 1 for stimulating abdominal muscles of a subject, and in particular, for stimulating the rectus abdominis, the transversalis and oblique muscles of the abdomen of the subject for toning of the muscles. Before describing the device 1 the position of the muscles in the abdominal wall of the subject will first be described with reference to FIG. 1.

Figure 1:
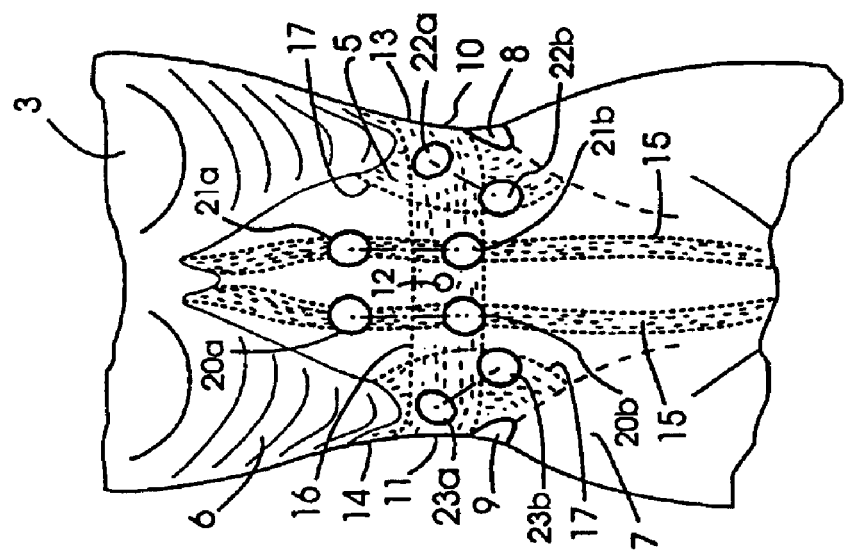
FIG. 1 is a front elevational view of a torso of a subject.
Figure 4:
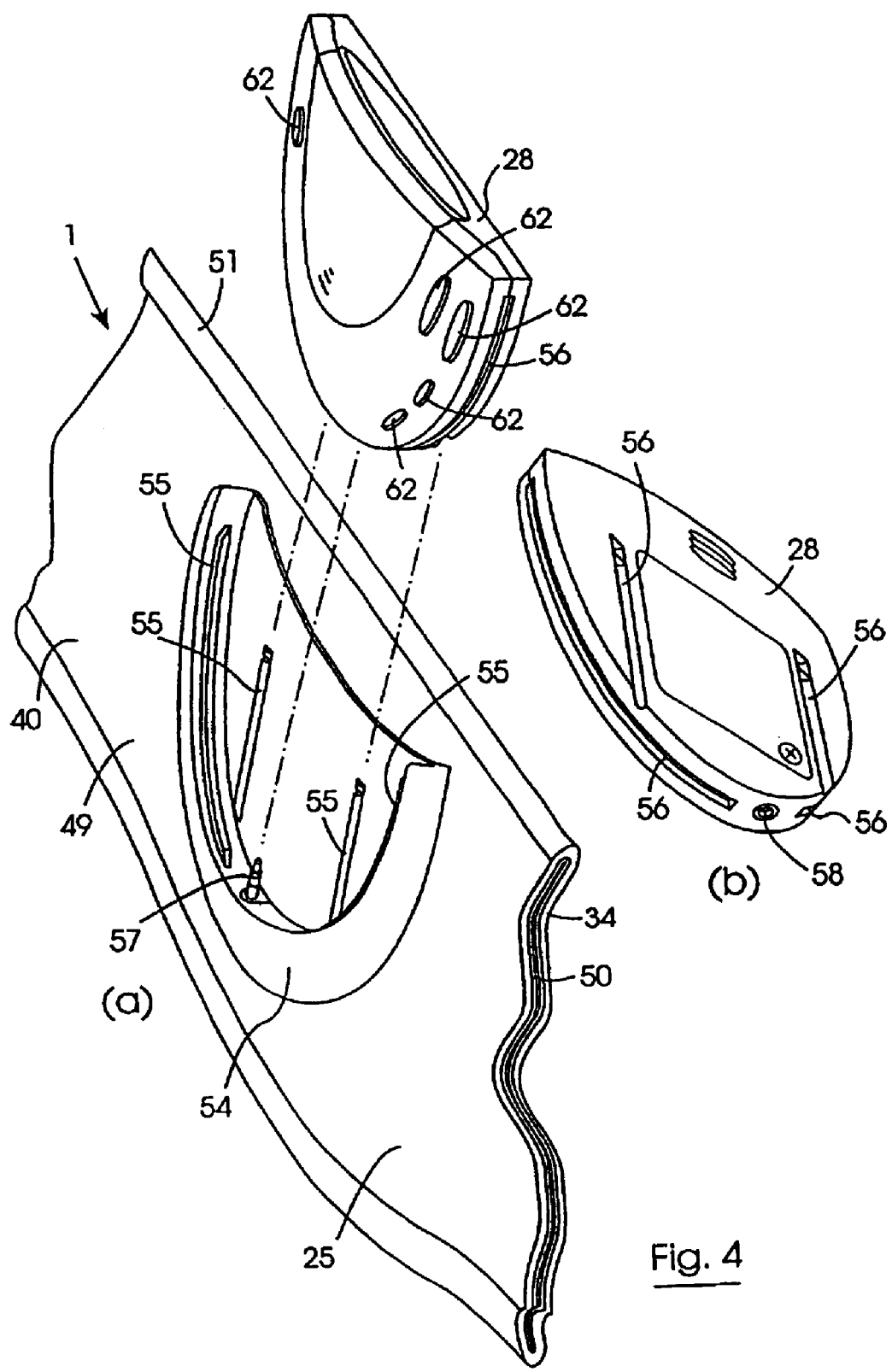
FIG. 4 is an exploded perspective view of a detail of the device of FIG. 2.

Referring now in particular to FIG. 1 a torso 3 of a subject is illustrated. The abdomen 5 of the subject is located between the rib cage 6 and the pelvis 7 and between the left and right iliac crests 8 and 9, respectively on the respective left and right sides 10 and 11, respectively of the subject. The umbilicus 12 is located centrally in the abdomen 5. The left and right mid-axillary lines 13 and 14 extend between the left and right iliac crests and the rib cage 6 on the left and right sides 10 and 11 of the torso 3. Rectus abdominis muscles which are indicated by the reference numeral 15 extend substantially longitudinally from a position below the rib cage 6 to a position above the pelvis, while the transversalis muscles which are indicated by the reference numeral 16 extend transversely across the abdomen between the left and right sides 10 and 11 thereof, while the oblique muscles indicated by the reference 17 extend obliquely between respective positions below the rib cage 6 to one side thereof and a central position adjacent the pelvis 7.

In known electrotherapeutic devices and methods, in order to stimulate these three muscles, namely, the rectus abdominis muscles 15, the transversalis muscles 16 and the oblique muscles 17 pulsed signals are applied to the abdomen of the subject through four electrode pairs 20a and 20b, 21a and 21b, 22a and 22b, 23a and 23b arranged as illustrated in FIG. 1. The electrode pairs 20a and 20b and 21a and 21b stimulate the rectus abdominis muscles 15, while the electrode pairs 22 and 23a and b stimulate the transversalis muscles and oblique muscles for toning thereof.

Referring now in particular to FIGS. 2 to 12 the device 1 comprises an attachment means, namely, a belt 25 for extending around the torso 3 of the subject for locating and retaining three electrodes, which in this embodiment of the invention are patch electrodes, namely, a central electrode 26 and a pair of side electrodes 27 adjacent the abdomen 5 for applying one or more pulsed signals generated by a signal generating means, namely, a signal generator 28 which is releasably located in the belt 25 as will be described below. A main locating means and two sets of secondary locating means provided respectively by main and secondary locating marks 29 and 30, respectively, are provided on an inner side 34 of the belt 25 for locating the central electrode 26 and the side electrodes 27, respectively on the belt 25.

The main locating marks 29 define two opposite peripheral sides of the central electrode 26 for defining a main locating area 31 for receiving and locating the central electrode 26 for accurately locating the central electrode 26 on the belt 25 to in use lie centrally over the umbilicus 12. In this embodiment of the invention each set of secondary locating marks 30a, 30b and 30c define three respective secondary locating areas 32a, 32b and 32c at which the respective side electrodes 27 may be selectively attached to the belt 25 so that in use the side electrodes preferably lie centrally over the corresponding one of the left and right mid-axillary lines 13 and 14 of the subject and on a mid-point which is substantially midway between the rib cage 6 and the corresponding one of the left and right iliac crests 8 and 9. Although in practice while it is desirable that the side electrodes 27 should line on the corresponding mid-axillary lines, it has been found that, in general, adequate stimulation of the muscles is achieved if the side electrodes 27 are located on the belt 25 to lie on respective lines extending from the umbilicus to the mid-point of the corresponding mid-axillary lines and towards the mid-axillary lines. In this embodiment of the invention the secondary locating marks 30a, 30b and 30c define a periphery 33 of one end of the corresponding side electrode 27 for indicating the three secondary locating areas 32a, 32b and 32c at which the side electrodes 27 may be located on the belt 25 for accommodating torsos of different girth about the waist.

The main locating area 31 and the secondary locating areas 32a, 32b and 32c are arranged on the belt 25 so that when the central electrode 26 is located in the main locating area 31, and the side electrodes 27 are located in the appropriate one of the secondary locating areas 32a, 32b or 32c, and when the belt 25 is secured around the torso 3 with the central electrode 26 located centrally over the umbilicus 12 the respective side electrodes 27 are located over the left and right mid-axillary lines 13 and 14, respectively, between the rib cage 6 and the left and right iliac crests 8 and 9, or relatively close to the mid-axillary lines.

A securing means, in this embodiment of the invention provided by hooks and eyes of the type typically sold under the Trade Mark VELCRO is provided at the respective ends 35 and 36 of the belt 25, a band of hooks 38 of the hooks and eyes being provided on the inner side 34 at the end 35, while bands of eyes 39 of the hooks and eyes are provided on the outer side 40 at the end 36 of the belt 25. In this embodiment of the invention four bands of eyes 39 are provided at spaced apart intervals for facilitating securing of the belt 25 to torsos 3 of different girth about the waist.

An electrically conductive main contact means, namely, an electrically conductive main contact 45 is located on the belt 25 centrally in the main locating area 31 for applying one or more pulsed signals generated by the signal generator 28 to the central electrode 26. A pair of secondary contact means provided by electrically connective secondary contacts 46 are located in the respective sets of secondary locating areas 32 for applying signals generated by the signal generator 28 to the respective side electrodes 27. Each secondary contact 46 is located in the sets of secondary locating areas 32 in such a way that irrespective of which of the secondary locating areas 32 is selected for receiving the side electrode 27 the side electrode 27 is always in contact with the corresponding secondary contact 46.

A reference means for locating the belt 25 relative to an anatomical reference, namely, the umbilicus in this embodiment of the invention is provided by the main locating area 31, and in turn the central electrode 26 for locating the belt 25 on the torso 3. The central electrode 26 when it is centrally located in the main locating area 31 is provided in a position so that when the belt 25 is secured to the torso 3 with the central electrode 26 centrally located on the umbilicus 12 the belt 25 is centrally located circumferentially and vertically on the torso 3. Thus, when the belt 25 is tightly secured around the torso 3 the side electrodes 27 are relatively accurately located over or relatively close to the mid-axillary lines 13 and 14 centrally between the rib cage 6 and the respective left and right iliac crests 8 and 9.

In order that the belt 25, and in turn the central and side electrodes 26 and 27 are tightly secured to the subject, and also to further accommodate varying girths of torso 3, the belt 25 is of a resilient elasticated material for facilitating stretching of the belt 25 between the respective ends 35 and 36. However, to further facilitate in accommodating torsos 3 of different girths, portions 47 between broken lines 48, see FIG. 3 of the belt 25 on respective opposite sides of the main locating area 29 and between the nearest secondary locating areas 32a are more resilient than the rest of the belt 25 for accommodating extra stretchability of the belt 25 in the resilient portions 47. This, further facilitates in aligning the side electrodes 27 with the respective left and right mid-axillary lines 13 and 14.

The belt 25 comprises a pair of outer layers 49 of stretchable textile material, and an inner layer 50 of stretchable foam material which are secured together by an edging braid 51 extending on respective opposite sides of the belt 25 and stitched to the outer layers 49 and the inner layer 50. The braid 51 is also of a stretchable material, and the stitching of the braid 51 to the outer and inner layers 49 and 50, respectively is arranged for providing greater stretchability in the resilient portions 47 than in the rest of the belt 25.

A receiving means in this embodiment of the invention provided by a receiving bracket 54 of plastics material is secured to the outer side 40 of the belt 25 for releasably securing the signal generator 28 to the belt 25. Guide tracks 55 in the receiving bracket 54 engage corresponding guide grooves 56 on the signal generator 28 with a snap fit action for releasably and securely retaining the signal generator 28 in the receiving bracket 54. A three contact jack plug 57 located in the receiving bracket 54 engages a corresponding three contact jack socket 58 in the signal generator 28 for connecting the signal generator 28 to the central and side electrodes 26 and 27.

Main and secondary connecting means, namely, main and secondary cables 59 and 60, respectively, extending from the jack plug 57 are respectively connected to the main contact 45 and the secondary contacts 46. The main and secondary cables 59 and 60 are located between the outer layers 49 of the belt 25, and the secondary cables 60 are provided in consertina shape for facilitating expansion of the resilient portions 47 of the belt 25. Control buttons 62 are provided on the signal generator 28 for operating corresponding control switches within the signal generator 28 for controlling the signals generated by the signal generator 28 as will be described below.

Turning now to the central and side electrodes 26 and 27, and referring in particular to FIGS. 7 to 9 the electrodes 26 and 27 are formed from electrically conductive foil 65. A first electrically conductive means comprising a first electrically conductive adhesive gel coating 67 is provided on one side 66 of the foil 65 for securing the respective central and side electrodes 26 and 27 to the belt 25 and for providing electrical continuity between the foil 65 of the electrodes 26 and 27 and the corresponding main or secondary contacts 45 and 46, respectively. A second electrically conductive means, namely, a secondary electrically conductive adhesive gel coating 68 is provided on the other side 69 of the foil 65 for adhering the electrodes 26 and 27 to the skin of the subject and for providing good electrical continuity between the respective electrodes 26 and 27 and the skin of the subject. In this embodiment of the invention in order to further enhance electrical continuity between the foil 65 of the electrodes 26 and 27 and the corresponding main and secondary contacts 45 and 46 the first adhesive coating 67 includes an electrolyte. Additionally, the adhesion strength of the first adhesive coating 67 to the belt 25 is greater than the adhesion of the second adhesive coating 66 to the skin of the subject for facilitating removal of the belt 25 and the electrodes 26 and 27 from the subject without causing detachment of the electrodes 26 and 27 from the belt 25.

In this embodiment of the invention the central electrode 26 is of dimensions 100 mm±20% in width in a circumferential direction about the torso 3, and 100 mm±50% height in a vertical direction. The side electrodes 27 are respectively of 75 mm height±20% by 100 mm wide±20%. Central and side electrodes 26 and 27 of these dimensions have been found to be of sufficient size so that the central electrode 26 when centrally applied over the umbilicus extends across a substantial portion of the rectus abdominis and the side electrodes 27 when located centrally on the mid-axillary lines 13 and 14 or relatively close thereto covers a sufficient area of the lower thoracic nerves and the first and second lumbar nerves for providing stimulation of the rectus abdominis muscles and the transversalis and oblique muscles.

The central and side electrodes 26 and 27 are supplied with release sheets (not shown) on respective opposite sides thereof for protecting the respective first and second adhesive coatings 67 and 68.

Referring now to FIGS. 13 to 18 various pulsed signals which can be generated by the signal generator 28 and various connections of the main and central electrodes 26 and 27 to the pulse generator 28 will now be described. Referring initially to FIGS. 13 and 14 in this connection configuration the respective left and right side electrodes 27a and 27b which are also designated with the reference letters L and R, respectively, are independently connected to the pulse generator 28, and independently apply respective pulsed signals $I_1$ and $I_2$ to the subject which are generated by the pulse generator 28. The central electrodes 26 which is designated in the reference letter U, acts as a common return electrode for returning the sum $I_3$ of the pulsed signals $I_1+I_2$ to the signal generator 28, where $I_3=I_1+I_2$. Accordingly, in this configuration the electrodes 26 and 27 are selected in pairs where one pair is formed by the central electrode 26 and one of the side electrodes 27, and the other pair is formed by the central electrode 26 and the other of the side electrodes 27. In other words the electrode pairs are the pairs R-U and L-U.

In this embodiment of the invention the duration of the pulses of each pulsed signal which is applied to the respective pairs of electrodes may be independently varied between 50 microseconds and 1000 microseconds. The interval between pulses of the pulsed signals may also be independently varied between 5 milliseconds and 1000 milliseconds. The magnitude M of the pulses of each pulsed signal $I_1$ and $I_2$ is independently variable by the signal generator 28, and may range from 0 mA to 100 mA. The pulses of the respective pulsed signals $I_1$ and $I_2$ are in phase, and thus, the pulses being returned to the signal generator 28 through the central electrodes 26 is the sum of the outgoing pulses $I_1$ and $I_2$.

Two of the control buttons 62 on the signal generator 28 provides for manual independent varying of the magnitude M of the pulses of the respective pulsed signals $I_1$ and $I_2$, and another of the buttons 62 on the signal generator 28 provides for balancing of the magnitude of the pulses of the respective pulsed signals. A further two of the buttons 62 on the signal generator 28 provides for varying the interval between pulses of the pulsed signals. The duration of the pulses of each pulsed signal is varied by another two of the buttons 62 on the signal generator 28. The control of the magnitude, the interval between the pulses and the duration of the pulses by the signal generator 28 will not be described further, since the generation and control of such pulsed signals will be well known to those skilled in the art.

FIGS. 15 and 16 illustrate an alternative connection configuration of the central and side electrodes 26 and 27 to the signal generator 28. In this configuration the electrodes 26 and 27 are selected in similar pairs as those described with reference to FIGS. 13 and 14, namely, the pairs R-U and L-U. However, only one pulsed signal $I_3$ is generated by the signal generator 28 and is applied to the two side electrodes 27a and 27b, and returned through the central electrode 26 which acts as a common return. In this embodiment of the invention the respective proportion $I_1$ and $I_2$ of the pulsed signals flowing through the side electrodes 27a and 27b may be similar or different, depending on the impedance between the respective side electrodes 27 and the central electrode 26 through the subject, and the impedance between the respective side electrodes 27 and the skin of the subject. The magnitude of the pulses are varied by one of the buttons 62 on the signal generator 28.

Referring now to FIGS. 17 and 18 there is illustrated a further alternative connection configuration of the central and side electrodes 26 and 27 to the signal generator 28, and alternative pulsed signals generated by the signal generator 28. In this configuration the electrodes 26 and 27 are selected in pairs similar to those described with reference to FIGS. 13 and 14, namely, the pairs R-U and L-U. The signal generator 28 generates two pulsed signals $I_1$ and $I_2$ which are applied respectively to the side electrodes 27a and 27b and are returned through the central electrode 26 which acts as a common return. The pulses of the pulsed signals $I_1$ and $I_2$ in this case are 180° out of phase with each other, however, the interval between the pulses of the respective pulsed signals is similar. The magnitude and duration of the pulses of the respective pulsed signals are independently variable, and as can be seen in FIG. 18 the pulses of the pulsed signal $I_1$ are of greater magnitude but shorter duration than the pulses of the pulsed signal $I_2$.

Figure 12:
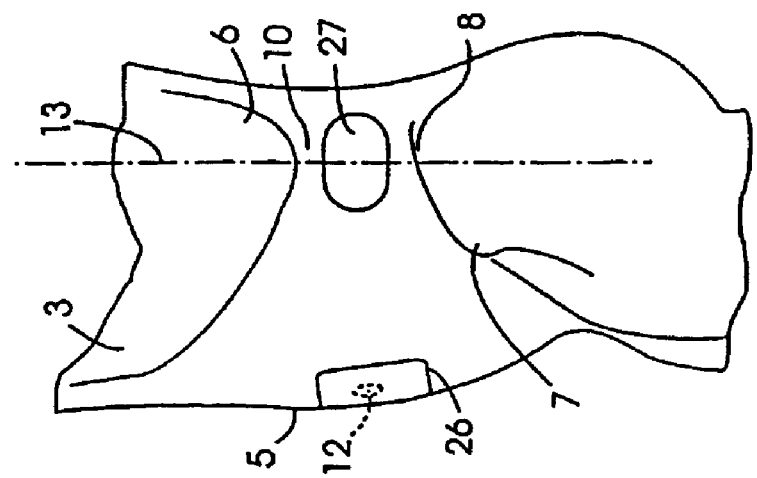
FIG. 12 is a side elevational view of the torso of the subject of FIG. 10 also illustrating the correct positioning of the electrodes of the device of FIG. 2.
Figure 11:
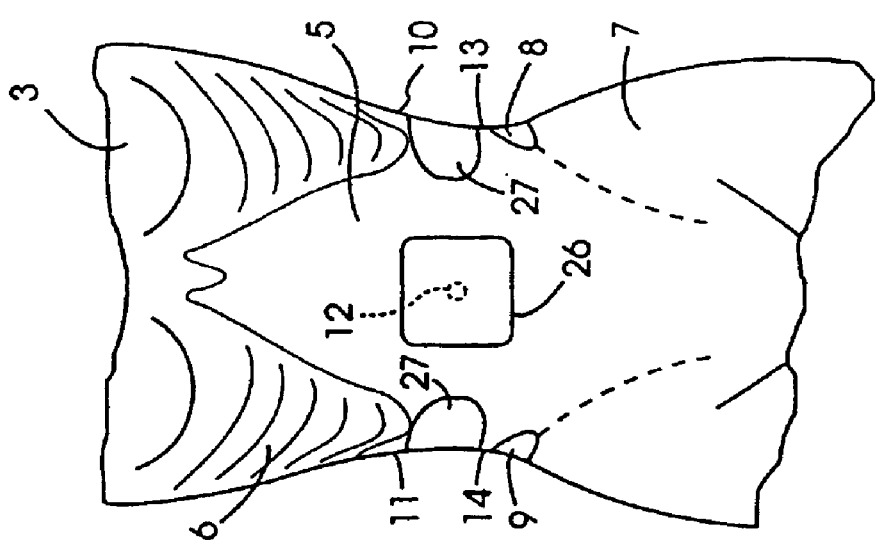
FIG. 11 is a front elevational view of the torso of the subject of FIG. 10 illustrating the correct positioning of the electrodes of the device of FIG. 2.
Figure 10:
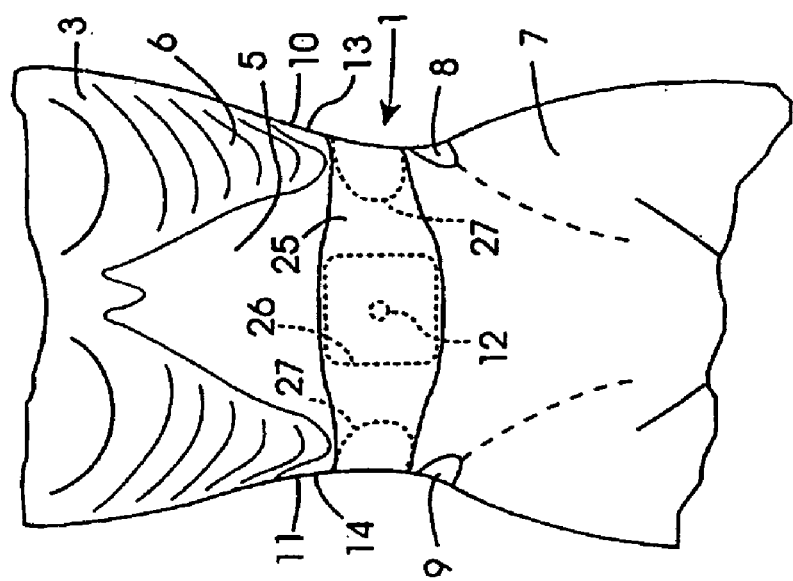
FIG. 10 is a front elevational view of a torso of a subject illustrating the device of FIG. 2 in use.
Figure 19:
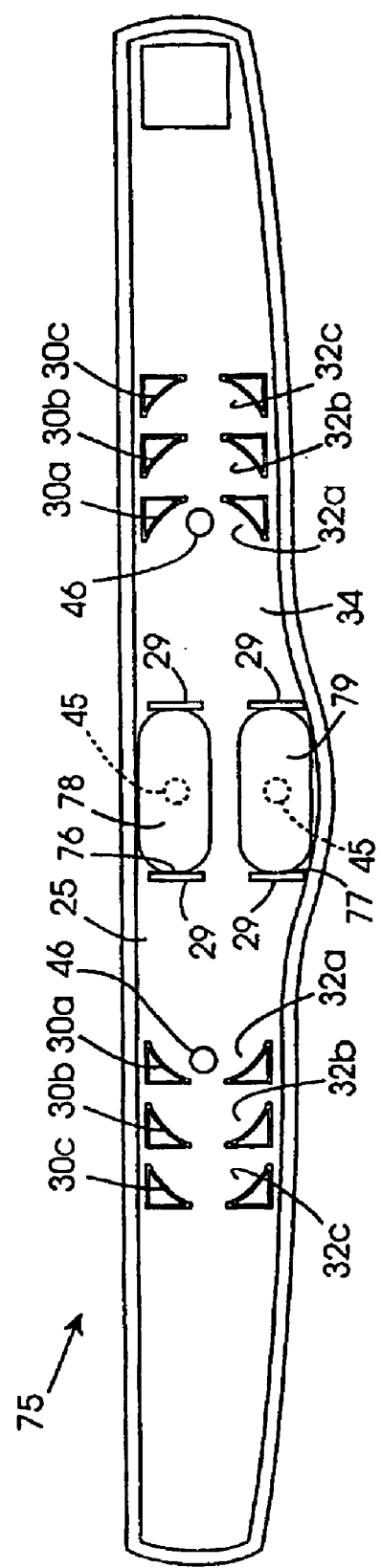
FIG. 19 is a rear plan view of a device according to another embodiment of the invention for stimulating abdominal muscles.

In use, with the belt 25 laid flat and the inner side 34 facing upwardly the central electrode 26 is secured centrally in the main locating area 31. The appropriate secondary locating area 32a, 32b or 32c is selected, depending on the girth of the torso 3 of the subject, and the respective side electrodes 27 are secured to the inner side 34 of the belt 25 with the peripheral edge 33 of the side electrodes 27 aligned with the appropriate secondary locating marks 30a, 30b or 30c. Remaining release sheets are then removed from the central and side electrodes 26 and 27 and the belt 25 is offered up to the torso 3 of the subject with the central electrode 26 centrally aligned with the umbilicus 12. The belt 25 is then stretched around the torso 3 of the subject until the side electrodes 27 are centrally aligned with the respective left and right mid-axillary lines centrally between the rib cage 6 and the respective left and right iliac crests or relatively close thereto. The belt 25 is then secured to the subject by the band of hooks 38 engaging the appropriate band 39 of eyes. FIGS. 11 and 12 illustrate the preferable locations of the central electrode 26 and the side electrodes 27 on the torso 3 when the belt 25 is tightly secured to the torso 3.

The signal generator 28 is then activated, and the desired pulsed signal or signals are selected. If the signal generator 28 is operated to provide two independent pulsed signals, the magnitude and/or duration of the pulses of the respective pulsed signals as the case may be is adjusted to the desired level, and the interval between pulses in certain cases may be adjusted. The pulsed signals may also be balanced as desired.

It has been surprisingly found that by centrally locating the central electrode 26 over the umbilicus so that the central electrode 26 extends around the umbilicus 12, and by providing the side electrodes 27 centrally aligned with the mid-axillary lines, centrally between the rib cage 6 and the corresponding left and right iliac crests, or between the umbilicus and the mid-axillary line towards the mid-axillary line, only three electrodes are required for providing adequate stimulation of the rectus abdominis muscle and the transversalis and oblique muscles for toning the muscles.

Referring now to FIGS. 19 to 27 there is illustrated a device according to another embodiment of the invention which is indicated generally by the reference numeral 75 for stimulating the abdominal muscles for toning thereof. The device 75 is substantially similar to the device 1, and similar components are identified by the same reference numerals. The main difference between the device 75 and the device 1 is that instead of providing a single main locating area, a pair of main locating areas, namely, a first main locating area 76 and a second main locating area 77 are provided for locating respective first and second central electrodes 78 and 79, respectively on the belt 25 for location respectively above and below the umbilicus 12. Otherwise, the device with the exception of the signal generator 28 is similar to the device 1. The first and second main locating areas 76 and 77, and in turn the first and second central electrodes 78 and 79 act as the reference means for locating the belt 25 on the torso 3. The belt 25 is located on the torso 3 with the umbilicus 12 located centrally between the respective first and second main locating areas 76 and 77, see FIGS. 20 and 21.

Referring now to FIGS. 22 to 27 alternative connecting configurations for connecting the electrodes 78, 79 and 27 to the signal generator 28 are illustrated for applying the pulsed signals to the subject through the electrodes 78, 79 and 27. The left and right side electrodes 27a and 27b are designated by the reference letters L and R, respectively, and the first and second central electrodes 78 and 79 are designated by the reference letters U1 and U2, respectively. In FIG. 22 the first and second electrodes 78 and 79 and the side electrodes 27 are connected such that the side electrodes 27 and the first central electrode 78 effectively form one single electrode, while the second electrode 79 forms the other electrode, namely, the return electrode. In the connecting configuration of FIG. 23 the electrodes 78, 79 and 27 are connected such that the side electrodes 27 are connected together and the first and second central electrodes 78 and 79 are independently connected to the signal generator 28. In this way the electrodes are selected in pairs such that one selected pair of electrodes is formed by the side electrodes 27 which effectively act as one electrode and the second central electrodes 79 which acts as a return electrode, and the other selected pair of electrodes comprises the first central electrode 78 and the second electrode 79, which also acts as a return electrode for that selected pair of electrodes. In other words the pairs of electrodes are the pairs (RL)-U2 and U1-U2. A first pulsed signal is applied to the selected electrode pair comprising the side electrodes 27 and the second central electrode 79, and a second pulsed signal is applied to the selected electrode pair comprising the first and second central electrode 78 and 79. The first and second pulsed signals may be identical or different and may be independently varied as discussed with reference to FIGS. 13, 14, 17 and 18.

Referring now to FIG. 24 there is illustrated a further alternative connection configuration of the first and second central electrodes 78 and 79 and the side electrodes 27 to the signal generator 28. In this configuration the electrodes are selected in the following pairs. One selected pair comprises the side electrodes 27a and 27b whereby one of the side electrodes, namely, the left side electrode 27a acts as the return electrode, and the other electrode pair is selected from the first and second central electrode 78 and 79, whereby the second central electrode 79 acts as the return electrode. In other words the electrode pairs are the pairs R-L and U1-U2. In this connection configuration the signal generator generates two pulsed signals independently of each other, one of which is applied to the subject through the side electrodes, while the other is applied to the subject through the first and second central electrodes 78 and 79. The two pulsed signals may be the same or different, however, in order to avoid a signal which is applied to the side electrode 27b being returned through the second electrode 79, and similarly, in order to avoid a signal applied to the first central electrodes 78 being returned through the side electrode 27a, the signals are multiplexed to the electrodes, and preferably, are 180° out of phase.

Figure 25:
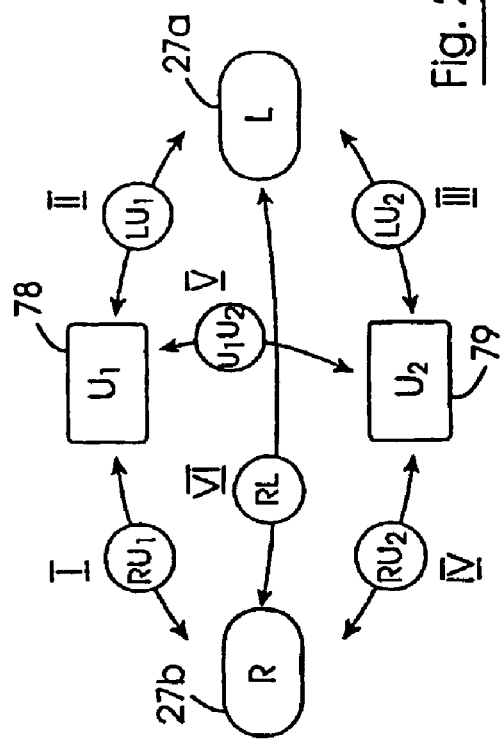
FIG. 25 is a diagrammatic representation of subcutaneous current paths which may be developed in the subject using the device of FIG. 19.
Figure 20:
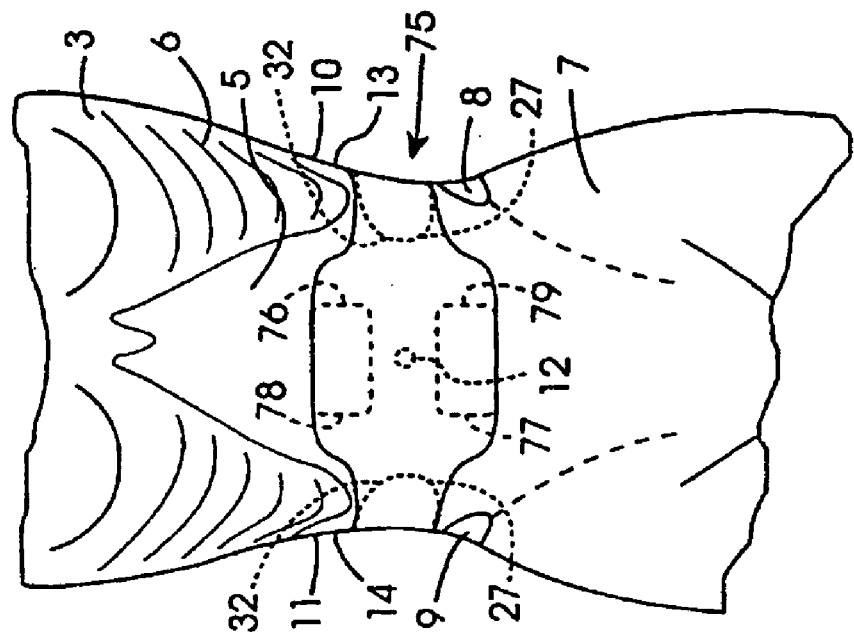
FIG. 20 is a front elevational view of a torso of a subject illustrating the device of FIG. 19 in use.
Figure 21:
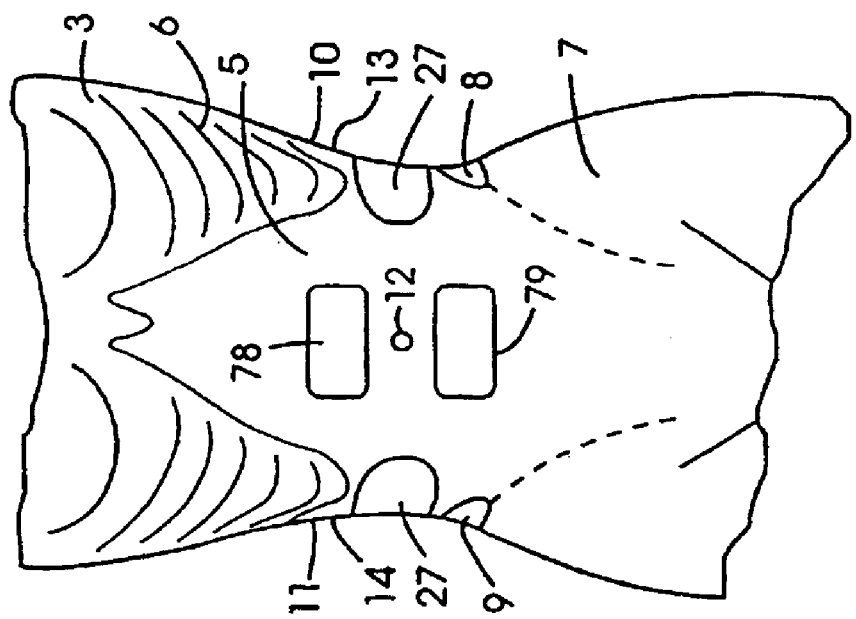
FIG. 21 is a front elevational view of the torso of the subject of FIG. 20 illustrating correct positioning of electrodes of the device of FIG. 19, FIGS. 22 to 24 are block representations of alternative configurations of the circuit of the device of FIG. 19.

Referring now to FIG. 25 there is illustrated a schematic representation of various electrode pairs which may be selectively selected from the first and second central electrodes 78 and 79 and the side electrodes 27 to the signal generator 28. In this embodiment of the invention the electrodes may be selectively selected in electrode pairs as follows:

| | |
|---|---|
| R-U1 | L-U2 |
| R-U2 | R-L |
| L-U1 | U1-U2 |

The subcutaneous currents which are passed through the subject between the respective first and second central electrodes 78 and 79 and the side electrodes 27 are illustrated in FIG. 25 and designated as RU1, LU1, RU2, LU2, RL and U1U2, and are also designated by the Roman numerals I to VI. The signals generated by the signal generator 28 may be applied to the first and second central electrodes 78 and 79 and the side electrodes 27 in any or all of the six electrode pairs, and may be applied sequentially, simultaneously, or partly simultaneously and sequentially to the electrode pairs in any order for selectively stimulating the abdominal muscles. The signals may be multiplexed to the selected electrode pairs, and the signals applied to the respective electrode pairs may be different for providing different stimulation to the various abdominal muscles.

Figure 26:
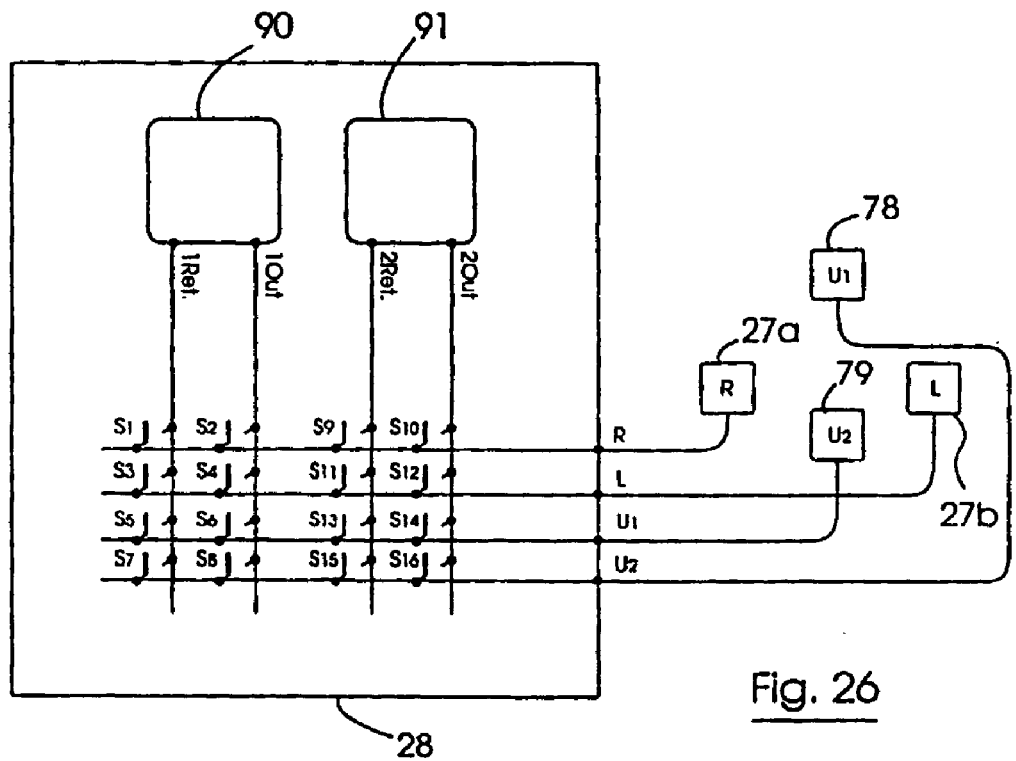
FIG. 26 is a block representation of one circuit configuration of the device of FIG. 19.

Referring now to FIG. 26 there is illustrated a circuit arrangement for applying signals to the subject through some or all of the electrode pairs selected from the electrodes 78, 79 and 27 described with reference to FIG. 25. In this embodiment of the invention the signal generator 28 is provided with a pair of pulse generators, namely, a first pulse generator 90 and a second pulse generator 91, which apply respective pulsed signals to the first and second central electrodes 78 and 79 and the side electrodes 27 through a selecting means, namely, a matrix of switches S1 to S16. The pulsed signal from the first pulse generator 90 s applied to the electrode 78, 79 and 27 through the switches S1 to S8, while the pulsed signal from the second pulse generator 91 is applied to the electrodes 78, 79 and 27 through the switches S9 to S16. A microprocessor (not shown) in the signal generator 28 selectively operates the switches S1 to S16 for selecting the electrode pairs and for applying the respective pulsed signals from the first and second pulse generators 90 and 91 to the first and second central electrodes 78 and 79 and the side electrodes 27 in some or all of the selected pairs described with reference to FIG. 25. The switches S1 to S16 may be relays or semiconductor switches, and in certain cases may be manually operated switches. The microprocessor (not shown) also controls the first and second pulse generators 90 and 91 for determining the signals to be generated by the respective pulse generators so that the signals outputted by the pulse generators 90 and 91 may be varied for applying different pulsed signals to the different selected pairs of electrodes for providing different levels of stimulation for the various muscles of the abdomen. Thus, the subcutaneous current paths through the subject are selectable by selecting the appropriate electrode pairs, and the signal to be passed through each current path is also selectable. Thus, the current distribution and effective pulse frequency at each electrode can be optimised for the tissue it is desired to stimulate.

Figure 27:
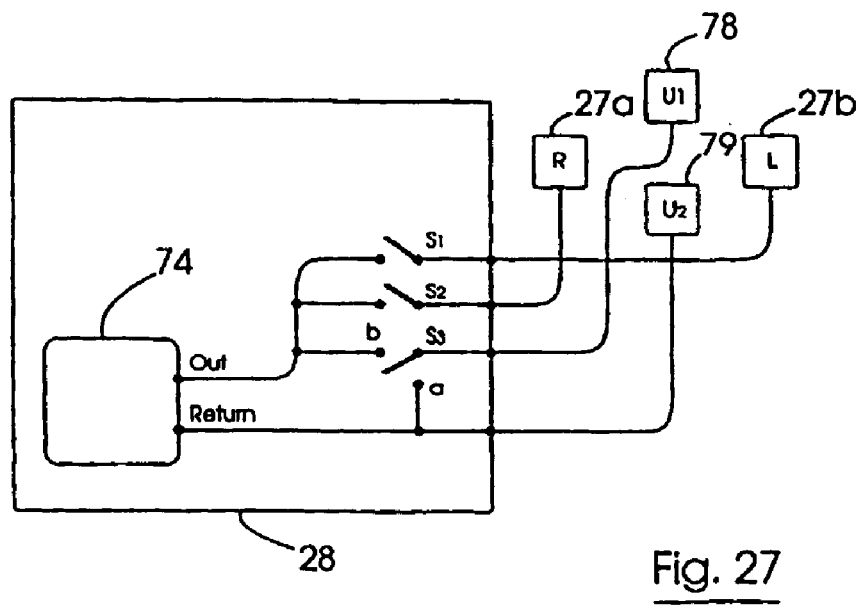
FIG. 27 is a block representation of an alternative circuit configuration of the device of FIG. 19.

FIG. 27 illustrates an alternative circuit arrangement for applying signals generated by the signal generator 28 to the first and second central electrodes 78 and 79 and the side electrodes 27. This circuit comprises a selecting means provided by switches S1, S2 and S3 for applying the signals generated by the signal generator 28 to the electrodes 78, 79 and 27. The switches S1, S2 and S3 provide for the selective selection of the electrodes in the following electrode pairs:

| | |
|---|---|
| R-U1 | R-U2 |
| L-U1 | U1-U2 |
| L-U2 | |

A microprocessor (not shown) in the signal generator 28 controls the switches S1, S2 and S3, and the pulsed signals are multiplexed from a pulse generator 74 within the signal generator 28 through the switches S1, S2 and S3 under the control of the microprocessor (not shown). The switches S1, S2 and S3 may be relays or semiconductor switches. When the switches S1 and S2 are closed, and the switch S3 is closed onto the contact (a) the current paths I, II, III and IV are enabled. When the switch S3 is closed onto the contact (b) the current path V is enabled. In this circuit arrangement there is no provision for selecting the electrode pair RL for providing the current path VI.

It has been found that by providing first and second central electrodes, with the first central electrode being located just above the umbilicus and the second central electrode located just below the umbilicus in certain circumstances stimulation of the rectus abdominis muscles is enhanced.

Referring now to FIGS. 28 to 30 there is illustrated a device according to a still further embodiment of the invention indicated generally by the reference numeral 80 for stimulating abdominal muscles of a subject The device 80 is substantially similar to the device 1, and similar components are identified by the same reference numerals. The main difference between the device 80 and the device 1 is that in this embodiment of the invention main and secondary fastening means comprising main and secondary stud fasteners 81 and 82 are provided for fastening the respective electrodes 26 and 27 to the main and secondary locating areas 31 and 32. In this embodiment of the invention each stud fastener 81 and 82 comprises a female part 83 and a male part 84. The male parts 84 are secured to and in electrical engagement with the electrodes 26 and 27, while the female parts 83 are secured to the belt 25 and provide electrical continuity between the electrodes 26 and 27 and the signal generator 28 through corresponding main and secondary cables 59 and 60.

In this embodiment of the invention one of the female parts 83 of the secondary stud fasteners 82 is provided in each of the three secondary locating areas 32a, 32b and 32c for receiving the male parts 84 with the corresponding side electrodes 27 in the desired secondary locating area 32. The female and male parts 83 and 84 of the stud fasteners 81 and 82 are of electrically conductive material, in this case chrome plated steel. An electrically insulating coating 85 is applied over a surface 86 of each female part 83 which is exposed, and which would be likely to come into contact with the skin of a subject if it were not covered by one of the side electrodes 27. This, thus, avoids any danger of a signal applied to the female part 83 of a secondary stud fastener 82 by the signal generator 28 being transferred directly to the subject from the surface 86 of the female part 83. However, the interior of a socket 87 of each female part 83 provides good electrical continuity with a corresponding male projection 88 from the corresponding male part 84 for ensuring electrical continuity between the female and male parts 83 and 84 of the stud fasteners 81 and 82.

Use of the device 80 is similar to that of FIG. 1 once the central and side electrodes 26 and 27 have been secured to the belt 25 by the stud fasteners 81 and 82.

While the central and side electrodes have been described as comprising an electrically conductive adhesive coating on the side of the electrodes for adhering the electrodes to the skin of the subject, it is envisaged in certain cases that the electrically conductive coating may be non-adhesive, and indeed, may be of the type which would provide a low friction surface. In certain cases, it is envisaged that such an electrically conductive coating may provide adequate electrical contact between the electrodes and the subject.

While the device has been described for stimulating abdominal muscles, it will be apparent to those skilled in the art that the device by suitably adapting the attachment means may be used for stimulating other muscle groups of a subject, for example, back muscles, leg muscles, arm muscles, or indeed any other muscle group.

It will of course be appreciated that as well as being able to vary the current, duration of the pulses, the interval between the pulses, and/or other parameters of the pulsed signal, the direction of the current through the subcutaneous paths of the subject may also be reversed. It will of course be appreciated that any or all of the subcutaneous current paths which may be selected by appropriately selecting the electrodes in appropriate selected pairs may be selected in any order, and the order and selection may vary during a treatment regime by suitably programming the microprocessor in the signal generator.

What is claimed is:

1. A device for attaching at least three electrodes to a subject for stimulating abdominal muscles of the subject, comprising:
    an attachment means for extending around the torso of the subject;
    at least three electrodes including at least one central electrode and two or more side electrodes;
    a central electrode marker on the attachment means for locating the a central electrode of the at least three electrodes adjacent the umbilicus of the subject; and
    two axiallary markers on the attachment means disposed on respective opposite sides of the central electrode marker for locating two corresponding side electrodes of the at least three electrodes spaced apart from the central electrode in a general direction towards a corresponding one of the right and left mid-axillary lines of the torso intermediate the rib cage and corresponding right and left iliac crests;
    whereby, by applying at least one pulsed signal to the subject through the respective central and side electrodes, abdominal muscles of the subject are stimulated.

2. The device as claimed in claim 1, wherein the axiallary markers are disposed on the attachment means for locating the respective side electrodes towards the mid-point of the corresponding mid-axillary line between the rib cage and the corresponding iliac crest.

3. The device as claimed in claim 1, wherein the axiallary markers are disposed on the attachment means for locating the respective side electrodes adjacent the corresponding mid-axillary line.

4. The device as claimed in claim 3, wherein the axiallary markers are disposed on the attachment means for locating the respective side electrodes adjacent the mid-point of the corresponding mid-axillary line between the rib cage and the corresponding iliac crest.

5. The device as claimed in claim 1, wherein the central electrode marker is disposed on the attachment means for locating the central electrode on the umbilicus and extending around the umbilicus.

6. The device as claimed in claim 1, wherein the central electrode marker is disposed on the attachment means for locating the central electrode on the umbilicus and extending completely around the umbilicus.

7. The device as claimed in claim 1, wherein the central electrode marker is disposed on the attachment means for locating the central electrode on the umbilicus, but with a greater area of the central electrode located below the umbilicus than above the umbilicus.

8. The device as claimed in claim 1, wherein the central electrode marker is disposed on the attachment means for locating the central electrode adjacent but not on the umbilicus.

9. The device as claimed in claim 1, wherein the central electrode marker is disposed on the attachment means for locating the central electrode below the umbilicus.

10. The device as claimed in claim 1, wherein the central electrode marker is disposed on the attachment means for locating the central electrode above the umbilicus.

11. The device as claimed in claim 1, wherein the central electrode marker is disposed on the attachment means for locating the central electrode both below and above the umbilicus.

12. The device as claimed claim 1, further comprising a reference means provided on the attachment means for locating the attachment means on the torso relative to an anatomical reference.

13. The device as claimed in claim 12, wherein the reference means is provided for locating the attachment means circumferentially around the torso.

14. The device as claimed in claim 12, wherein the reference means is provided for locating the attachment means vertically along the torso.

15. The device as claimed in claim 12, wherein the central electrode marker acts as the reference means for locating the attachment means relative to the anatomical reference provided by the umbilicus.

16. The device as claimed in claim 1, wherein the central electrode marker comprises a first central electrode marker and a second central electrode marker for locating respective corresponding first and second central electrodes adjacent the umbilicus of the subject.

17. The device as claimed in claim 16, wherein the first central electrode marker is provided for locating the first central electrode above the umbilicus, and the second central electrode marker is provided for locating the second central electrode below the umbilicus.

18. The device as claimed in claim 1, further comprising two sets of at least two axiallary markers disposed on the respective opposite sides of the central electrode marker for facilitating selective location of the respective side electrodes for accommodating different girths of torso.

19. The device as claimed in claim 18, wherein each set of axiallary markers comprises three axillary markers.

20. The device as claimed in claim 1, wherein portions of the attachment means on respective opposite sides of the central electrode marker between the central electrode marker and the corresponding axiallary markers are formed of resilient material for facilitating resilient stretching of the attachment means between the central electrode and corresponding axillary markers.

21. The device as claimed in claim 1, wherein the attachment means is formed of a resilient material for facilitating stretching of the attachment means around the torso, the resilient portions of the attachments means being of greater stretchability than that of the rest of the attachment means.

22. The device as claimed in claim 1, further comprising a main electrically conductive contact means provided on the attachment means corresponding to each central electrode marker for receiving the at least one pulsed signal and for relaying the signal to the corresponding central electrode.

23. The device as claimed in claim 22, wherein each main contact means is located within the corresponding central electrode marker.

24. The device as claimed in claim 1, further comprising two secondary electrically conductive contact means provided on the attachment means for receiving the at least one pulsed signal and for relaying the signal to the respective corresponding side electrodes.

25. The device as claimed in claim 24, wherein each secondary contact means is located adjacent the corresponding axiallary marker or the corresponding set of axiallary markers.

26. The device as claimed in claim 24, wherein each secondary contact means is located adjacent the corresponding axiallary markers so that irrespective of which axiallary markers is selected for locating the corresponding side electrode the side electrode is in electrically conductive engagement with the secondary contact means.

27. The device as claimed in claim 1, wherein each central electrode and axiallary markers is provided as a visually perceptive marker means.

28. The device as claimed in claim 1, wherein each central electrode and axiallary markers is formed as a corresponding locating mark on the attachment means.

29. The device as claimed in claim 28, wherein each locating mark defines an outline of a part of the periphery of the corresponding electrode corresponding to the central and axiallary markers.

30. The device as claimed in claim 28, wherein each central and axiallary markers are adapted for locating a patch type electrode.

31. The device as claimed in claim 1, wherein the at least three electrodes are formed as a removable part of the device.

32. The device as claimed in claim 31, wherein each electrode is a patch type electrode.

33. The device as claimed in claim 31, wherein each side electrode is sized to cover at least a portion of the corresponding lower thoracic nerves and the corresponding first and second lumbar nerves.

34. The device as claimed in claim 31, wherein each central electrode is sized to extend substantially across the rectus abdominus muscle.

35. The device as darned in claims 31, wherein each electrode defines an area of contact over which the electrode makes direct electrical contact with the subject, the area of contact of each side electrode being such as not to exceed the area of contact of the or both central electrodes.

36. The device as claimed in claim 35, wherein the area of contact of each side electrode does not exceed one third of the area of contact of the central electrode.

37. The device as claimed in claim 35, wherein each side electrode is of width in a circumferential direction relative to the torso of the subject in the range of 50 mm to 150 mm, and is of length in a vertical direction relative to the torso of the subject in the range of 80 mm to 120 mm.

38. The device as claimed in claim 31, further comprising a first electrically conductive coating provided on one side of each electrode for electrically connecting the electrode to the corresponding contact means.

39. The device as claimed in claim 38, wherein the first coating is a gel type coating containing an electrolyte solution for enhancing electrical contact between the electrode and the corresponding contact means.

40. The device as claimed in claim 38, further comprising a second electrically conductive coating provided on the other side of each electrode for electrically connecting the electrode to the torso of the subject.

41. The device as claimed in claim 40, wherein the second coating is a gel type coating.

42. The device as claimed in claim 40, wherein the second coating is an adhesive coating.

43. The device as claimed in claim 40, wherein the first coating is an adhesive coating.

44. The device as claimed in claim 43, wherein the bond strength of the first coating to the attachment means is greater than the bond strength of the second coating to the torso for facilitating removal of the attachment means and the electrodes located thereon from the torso of the subject.

45. The device as claimed in claim 40, wherein the electrodes are pre-coated with the respective first and second coatings.

46. The device as claimed in claim 1, further comprising a receiving means provided in the attachment means for receiving a signal generating means for generating the at least one pulsed signal.

47. The device as claimed in claim 46, further comprising a main electrical connecting means extending between the receiving means and each main contact means for relaying the at least one pulsed signal from the signal generating means to the corresponding main contact means.

48. The device as claimed in claim 47, further comprising a secondary electrical connecting means extends between the receiving means and each secondary contact means for relaying the at least one pulsed signal from the signal generating means to the corresponding secondary contact means.

49. The device as claimed in claim 48, wherein each electrical connecting means is located within the attachment means.

50. The device as claimed claim 46, wherein the receiving means is a releasable receiving means for releasably receiving the signal generating means.

51. The device as claimed in claim 50, wherein the receiving means receives the signal generating means with a snap fit action.

52. The device as claimed in claim 1, wherein the attachment means comprises a belt.

53. The device as claimed in claim 52, further comprising a securing means provided on the belt for securing the belt around the torso of the subject.

54. The device as claimed in claim 1, further comprising a main fastening means provided corresponding to each central electrode marker for fastening a corresponding central electrode to the attachment means adjacent the corresponding central electrode marker.

55. The device as claimed in claim 54, further comprising two secondary fastening means provided in the attachment means for fastening the respective side electrodes to the attachment means adjacent the corresponding selected axiallary markers.

56. The device as claimed in claim 55, wherein each fastening means comprises a stud fastener.

57. The device as claimed in claim 56, wherein each stud fastener comprises a female part and a male part, the female part being secured to the attachment means.

58. The device as claimed in claim 57, wherein each stud fastener is electrically conductive so that the female part of the stud fasteners form the corresponding contact means.

59. The device as claimed in claim 57, wherein an exposed surface of the female part of each stud fastener is of electrically insulating material.

60. The device as claimed in claim 59, wherein the exposed surface of each female part of each stud fastener is coated with an electrically insulating coating.

61. The device as claimed in claim 56, wherein the stud fastener comprises a male part for attaching to a corresponding electrode, and a female part for attaching to the attachment means.

62. The device as claimed in claim 61, wherein the male and female parts of the stud fastener engage each other with electrically conductive engagement.

63. The device as claimed in claim 61, wherein an exposed external surface of the female part of the stud fastener which abuts the male part of the stud fastener is of electrically insulating material.

64. The device as claimed in claim 63, wherein the electrically insulating material is provided by an electrically insulated coating on the exposed abutting surface.

* * * * *